(12) United States Patent
McClintock et al.

(10) Patent No.: US 9,125,703 B2
(45) Date of Patent: Sep. 8, 2015

(54) ROD REDUCER, COMPRESSOR, DISTRACTOR SYSTEM

(71) Applicant: K2M, Inc., Leesburg, VA (US)

(72) Inventors: Larry McClintock, Gore, VA (US); Clint Boyd, Winchester, VA (US)

(73) Assignee: K2M, Inc., Leesburg, VA (US)

( * ) Notice: Subject to any disclaimer, the term of this patent is extended or adjusted under 35 U.S.C. 154(b) by 200 days.

(21) Appl. No.: 13/741,934

(22) Filed: Jan. 15, 2013

(65) Prior Publication Data

US 2013/0184763 A1    Jul. 18, 2013

Related U.S. Application Data

(60) Provisional application No. 61/586,928, filed on Jan. 16, 2012.

(51) Int. Cl.
*A61B 17/70* (2006.01)
*A61B 17/88* (2006.01)

(52) U.S. Cl.
CPC .............. *A61B 17/88* (2013.01); *A61B 17/708* (2013.01); *A61B 17/7079* (2013.01); *A61B 17/7086* (2013.01)

(58) Field of Classification Search
CPC ............ A61B 17/025; A61B 17/7074; A61B 17/7083; A61B 17/7085; A61B 17/7086; A61B 17/0256
USPC ........... 606/246, 279, 86 A, 86 R, 90, 99, 105
See application file for complete search history.

(56) References Cited

U.S. PATENT DOCUMENTS

| | | | | |
|---|---|---|---|---|
| 1,920,821 | A | * | 8/1933 | Wassenaar .................. 606/86 R |
| 3,244,170 | A | * | 4/1966 | McElvenny .................... 606/71 |
| 4,263,899 | A | | 4/1981 | Burgin |
| 5,167,662 | A | * | 12/1992 | Hayes et al. .................. 606/916 |
| 5,529,571 | A | | 6/1996 | Daniel |
| 5,685,826 | A | | 11/1997 | Bonutti |
| 5,944,658 | A | | 8/1999 | Koros et al. |
| 6,123,707 | A | | 9/2000 | Wagner |
| 6,200,322 | B1 | | 3/2001 | Branch et al. |
| 6,616,605 | B2 | | 9/2003 | Wright et al. |
| 6,849,064 | B2 | | 2/2005 | Hamada |
| 6,929,606 | B2 | | 8/2005 | Ritland |
| 7,011,660 | B2 | | 3/2006 | Sherman et al. |
| 7,083,621 | B2 | | 8/2006 | Shaolian et al. |
| 7,160,300 | B2 | | 1/2007 | Jackson |

(Continued)

*Primary Examiner* — Eduardo C Robert
*Assistant Examiner* — Michelle C Eckman
(74) *Attorney, Agent, or Firm* — Carter, Deluca, Farrell & Schmidt, LLP

(57) ABSTRACT

A compressor/distractor system for operating on a spine is disclosed. The system includes two rod reducers which each advance a spinal rod into the shoulder portion of a pedicle screw. Each rod reducer includes an inner member, an outer member, and a pair of gripping members. Each outer member receives and advances the spinal rod into the pedicle screw. The outer member also includes a through slot which receives the proximal end of each of the pair of gripping members which may limit the longitudinal translation of the outer member with respect to the inner member. The compressor/distractor system may include a compressor/distractor device which has a compressing, a distracting, and a neutral configuration. A method for using the minimally invasive rod reducers with the compressor/distractor system to secure at least two pedicle screws in desired positions on a spinal rod is also disclosed.

12 Claims, 11 Drawing Sheets

(56) References Cited

U.S. PATENT DOCUMENTS

| | | | |
|---|---|---|---|
| 7,179,261 B2 | 2/2007 | Sicvol et al. | |
| 7,188,626 B2 | 3/2007 | Foley et al. | |
| 7,250,052 B2 | 7/2007 | Landry et al. | |
| 7,462,182 B2 | 12/2008 | Lim | |
| 7,491,208 B2 | 2/2009 | Pond, Jr. et al. | |
| 7,591,836 B2 | 9/2009 | Dick et al. | |
| 7,625,379 B2 | 12/2009 | Puno et al. | |
| 7,651,502 B2 | 1/2010 | Jackson | |
| 7,655,008 B2 | 2/2010 | Lenke et al. | |
| 7,666,189 B2 | 2/2010 | Gerber et al. | |
| 7,794,464 B2 * | 9/2010 | Bridwell et al. | 606/86 A |
| 7,854,751 B2 | 12/2010 | Sicvol et al. | |
| 7,922,749 B2 | 4/2011 | Dewey | |
| 7,927,334 B2 | 4/2011 | Miller et al. | |
| 7,946,982 B2 | 5/2011 | Hamada | |
| 7,951,168 B2 * | 5/2011 | Chao et al. | 606/246 |
| 7,951,175 B2 * | 5/2011 | Chao et al. | 606/279 |
| 7,955,355 B2 | 6/2011 | Chin | |
| 7,981,115 B2 * | 7/2011 | Justis et al. | 606/102 |
| 7,988,694 B2 | 8/2011 | Barrus et al. | |
| 8,002,798 B2 | 8/2011 | Chin et al. | |
| 8,007,516 B2 * | 8/2011 | Chao et al. | 606/246 |
| 8,147,524 B2 | 4/2012 | Piza Vallespir | |
| 8,192,438 B2 | 6/2012 | Garamszegi | |
| 8,206,395 B2 * | 6/2012 | McLean et al. | 606/86 A |
| 8,221,426 B2 * | 7/2012 | Justis et al. | 606/86 A |
| 8,221,474 B2 * | 7/2012 | Bridwell et al. | 606/279 |
| 8,230,863 B2 | 7/2012 | Ravikumar et al. | |
| 8,277,453 B2 * | 10/2012 | Kave et al. | 606/86 A |
| 8,298,138 B2 | 10/2012 | Gorek et al. | |
| 8,303,595 B2 | 11/2012 | Jones | |
| 8,308,729 B2 | 11/2012 | Nunley et al. | |
| 8,308,774 B2 * | 11/2012 | Hoffman et al. | 606/279 |
| 8,545,505 B2 * | 10/2013 | Sandstrom et al. | 606/86 A |
| 8,702,713 B2 * | 4/2014 | Nayet et al. | 606/86 A |
| 8,764,757 B1 * | 7/2014 | Tumialan | 606/86 A |
| 8,784,424 B2 * | 7/2014 | Tsuang et al. | 606/86 A |
| 2002/0052603 A1 | 5/2002 | Nichols et al. | |
| 2004/0230191 A1 | 11/2004 | Frey et al. | |
| 2004/0267275 A1 | 12/2004 | Cournoyer et al. | |
| 2005/0131422 A1 * | 6/2005 | Anderson et al. | 606/104 |
| 2005/0245928 A1 * | 11/2005 | Colleran et al. | 606/61 |
| 2006/0004380 A1 * | 1/2006 | DiDomenico et al. | 606/105 |
| 2006/0200132 A1 * | 9/2006 | Chao et al. | 606/61 |
| 2006/0247645 A1 * | 11/2006 | Wilcox et al. | 606/86 |
| 2006/0247649 A1 * | 11/2006 | Rezach et al. | 606/90 |
| 2006/0264934 A1 * | 11/2006 | Fallin | 606/61 |
| 2007/0055247 A1 | 3/2007 | Jahng | |
| 2007/0162009 A1 * | 7/2007 | Chao et al. | 606/61 |
| 2007/0162010 A1 * | 7/2007 | Chao et al. | 606/61 |
| 2007/0233079 A1 * | 10/2007 | Fallin et al. | 606/61 |
| 2008/0015601 A1 | 1/2008 | Castro et al. | |
| 2008/0077155 A1 * | 3/2008 | Diederich et al. | 606/105 |
| 2008/0119862 A1 * | 5/2008 | Wicker et al. | 606/99 |
| 2008/0125789 A1 * | 5/2008 | Butters et al. | 606/105 |
| 2008/0172062 A1 * | 7/2008 | Donahue et al. | 606/104 |
| 2009/0018593 A1 | 1/2009 | Barrus et al. | |
| 2009/0062857 A1 * | 3/2009 | Ramsay et al. | 606/246 |
| 2009/0082775 A1 * | 3/2009 | Altarac et al. | 606/90 |
| 2009/0138056 A1 * | 5/2009 | Anderson et al. | 606/86 A |
| 2009/0143828 A1 * | 6/2009 | Stad et al. | 606/86 A |
| 2009/0149892 A1 * | 6/2009 | Stad et al. | 606/86 A |
| 2009/0157125 A1 * | 6/2009 | Hoffman et al. | 606/86 A |
| 2009/0228053 A1 * | 9/2009 | Kolb et al. | 606/86 A |
| 2009/0259262 A1 * | 10/2009 | Nayet | 606/86 A |
| 2009/0326586 A1 * | 12/2009 | Duarte | 606/264 |
| 2010/0024487 A1 * | 2/2010 | Khoo et al. | 66/90 |
| 2010/0030283 A1 * | 2/2010 | King et al. | 606/86 A |
| 2010/0324610 A1 * | 12/2010 | Bridwell et al. | 606/86 A |
| 2010/0331849 A1 * | 12/2010 | Riesinger et al. | 606/90 |
| 2011/0077690 A1 * | 3/2011 | Shin et al. | 606/278 |
| 2011/0106082 A1 * | 5/2011 | Kave et al. | 606/70 |
| 2011/0137358 A1 * | 6/2011 | Manninen | 606/86 R |
| 2011/0152940 A1 * | 6/2011 | Frigg et al. | 606/264 |
| 2011/0172714 A1 | 7/2011 | Boachie-Adjei et al. | |
| 2011/0172723 A1 * | 7/2011 | Miller et al. | 606/86 A |
| 2011/0196426 A1 * | 8/2011 | Peukert et al. | 606/279 |
| 2011/0257692 A1 * | 10/2011 | Sandstrom et al. | 606/86 A |
| 2011/0282402 A1 * | 11/2011 | Chao et al. | 606/86 A |
| 2011/0295328 A1 * | 12/2011 | Woolley et al. | 606/86 A |
| 2011/0313477 A1 * | 12/2011 | McLean et al. | 606/86 A |
| 2011/0319938 A1 * | 12/2011 | Piza Vallespir et al. | 606/264 |
| 2012/0031792 A1 * | 2/2012 | Petit | 206/438 |
| 2012/0035668 A1 * | 2/2012 | Manninen et al. | 606/305 |
| 2012/0078308 A1 * | 3/2012 | Dziedzic et al. | 606/264 |
| 2012/0083853 A1 * | 4/2012 | Boachie-Adjei et al. | 606/86 A |
| 2012/0116467 A1 * | 5/2012 | King et al. | 606/86 A |
| 2012/0191137 A1 * | 7/2012 | Butters et al. | 606/279 |
| 2012/0191143 A1 * | 7/2012 | Nayet et al. | 606/86 A |
| 2012/0197297 A1 * | 8/2012 | Bootwala et al. | 606/246 |
| 2012/0239096 A1 * | 9/2012 | Gleeson et al. | 606/86 A |
| 2012/0239097 A1 * | 9/2012 | Garamszegi | 606/86 A |
| 2012/0271365 A1 * | 10/2012 | Daubs et al. | 606/86 A |
| 2012/0323279 A1 * | 12/2012 | Tsuang et al. | 606/279 |
| 2013/0012999 A1 * | 1/2013 | Petit | 606/279 |
| 2013/0046345 A1 * | 2/2013 | Jones et al. | 606/266 |
| 2013/0096637 A1 * | 4/2013 | Richelsoph et al. | 606/86 A |
| 2013/0110184 A1 * | 5/2013 | Wing et al. | 606/86 A |
| 2013/0172947 A1 * | 7/2013 | Greenberg | 606/86 A |
| 2013/0184763 A1 * | 7/2013 | McClintock et al. | 606/279 |
| 2013/0238037 A1 * | 9/2013 | Stad et al. | 606/86 A |
| 2013/0245692 A1 * | 9/2013 | Hayes et al. | 606/279 |
| 2013/0245694 A1 * | 9/2013 | Choi et al. | 606/279 |
| 2013/0274804 A1 * | 10/2013 | Hutton et al. | 606/264 |
| 2013/0289633 A1 * | 10/2013 | Gleeson et al. | 606/86 A |
| 2014/0018860 A1 * | 1/2014 | Butters et al. | 606/279 |
| 2014/0031828 A1 * | 1/2014 | Patel et al. | 606/90 |
| 2014/0039557 A1 * | 2/2014 | Stad et al. | 606/279 |
| 2014/0039567 A1 * | 2/2014 | Hoefer et al. | 606/86 A |
| 2014/0046372 A1 * | 2/2014 | Ibrahim et al. | 606/250 |
| 2014/0052139 A1 * | 2/2014 | Manninen | 606/105 |
| 2014/0074106 A1 * | 3/2014 | Shin | 606/104 |
| 2014/0074171 A1 * | 3/2014 | Hutton et al. | 606/279 |
| 2014/0100617 A1 * | 4/2014 | Sandstrom et al. | 606/86 A |
| 2014/0100618 A1 * | 4/2014 | Kolb et al. | 606/86 A |
| 2014/0107707 A1 * | 4/2014 | Rovner | 606/264 |
| 2014/0114354 A1 * | 4/2014 | May et al. | 606/246 |
| 2014/0135855 A1 * | 5/2014 | Jones et al. | 606/86 A |
| 2014/0163575 A1 * | 6/2014 | Thoren et al. | 606/105 |
| 2014/0188182 A1 * | 7/2014 | Chao et al. | 606/86 R |
| 2014/0249591 A1 * | 9/2014 | Peultier et al. | 606/86 A |
| 2014/0257312 A1 * | 9/2014 | Solitario et al. | 606/90 |
| 2014/0277198 A1 * | 9/2014 | Stad | 606/86 A |
| 2014/0316475 A1 * | 10/2014 | Parikh et al. | 606/86 A |

* cited by examiner

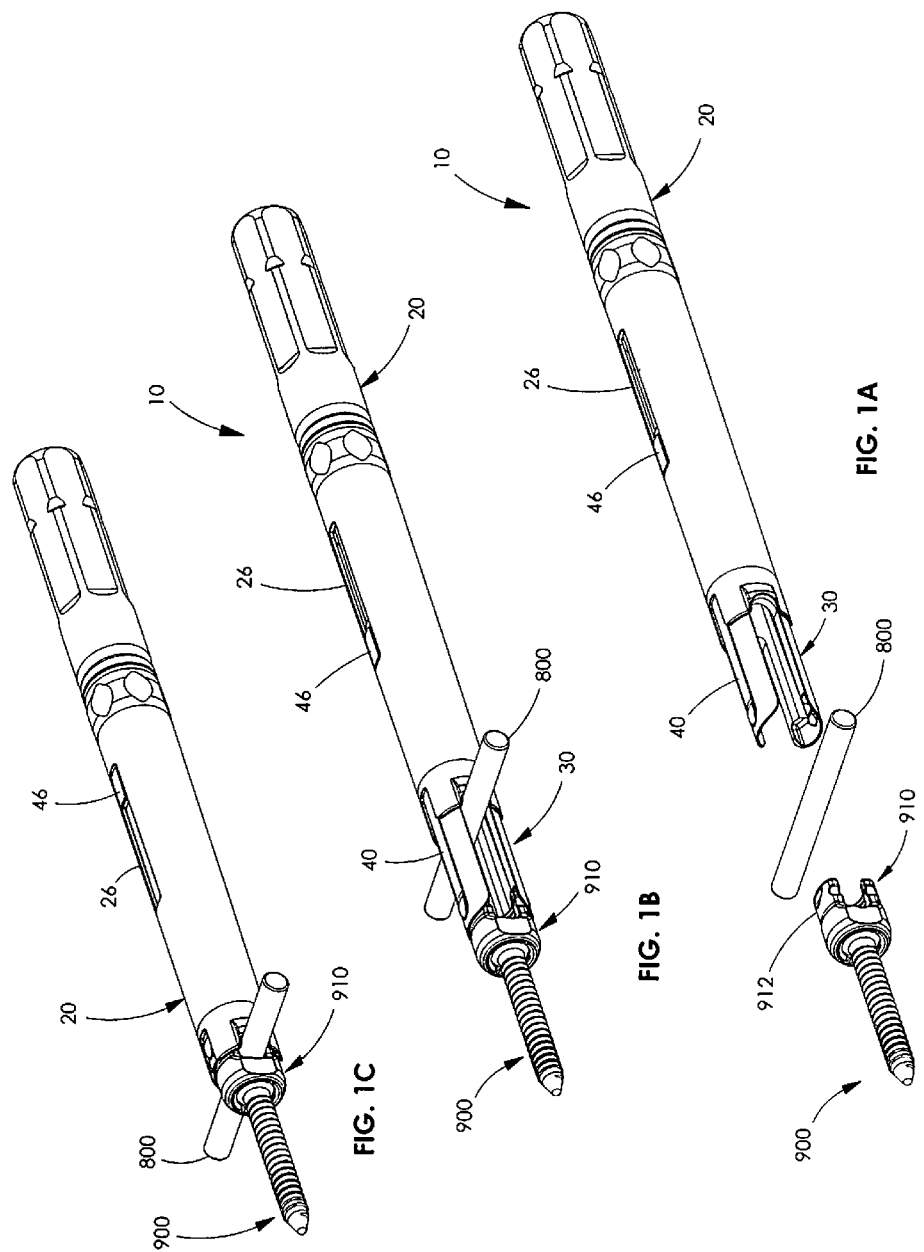

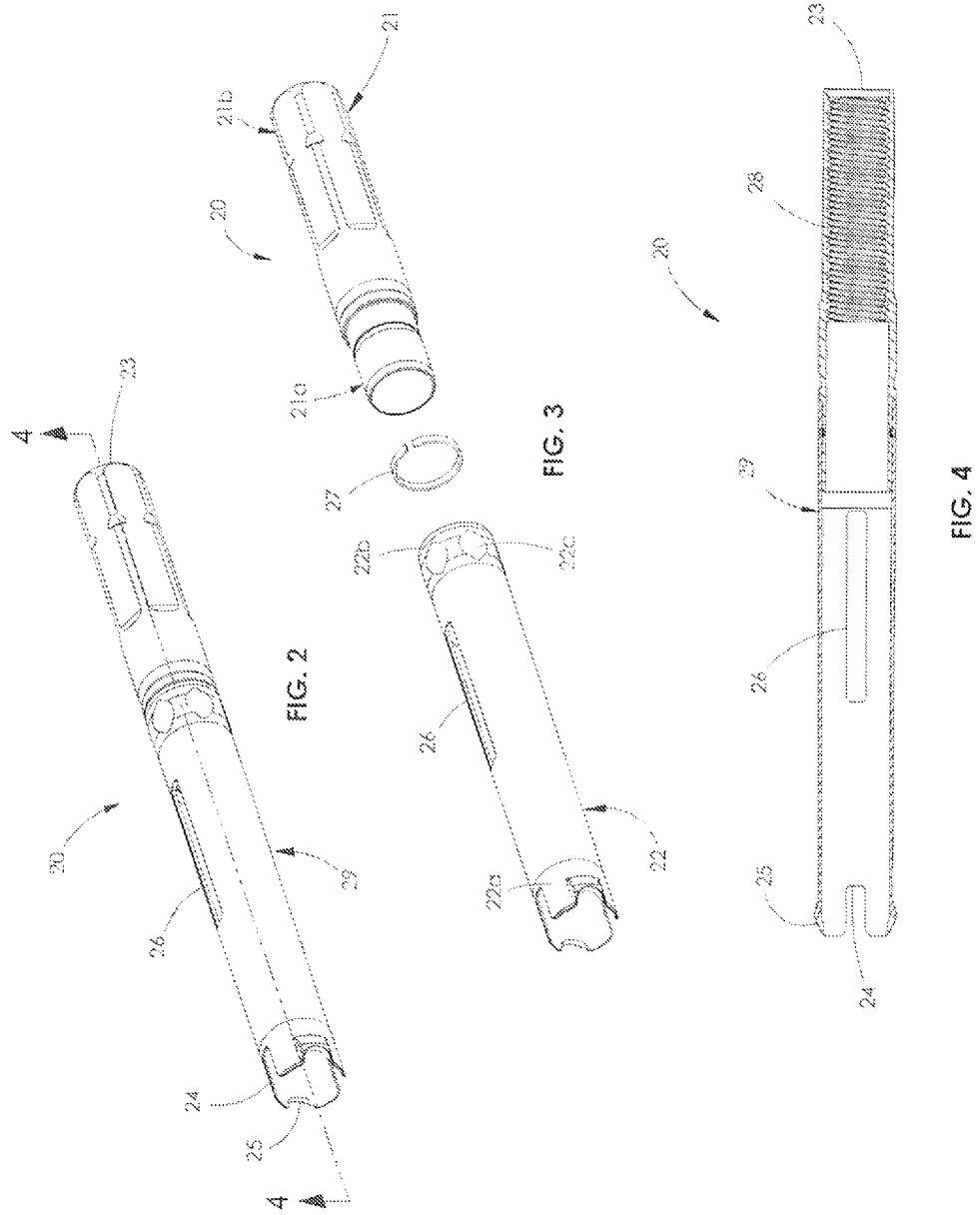

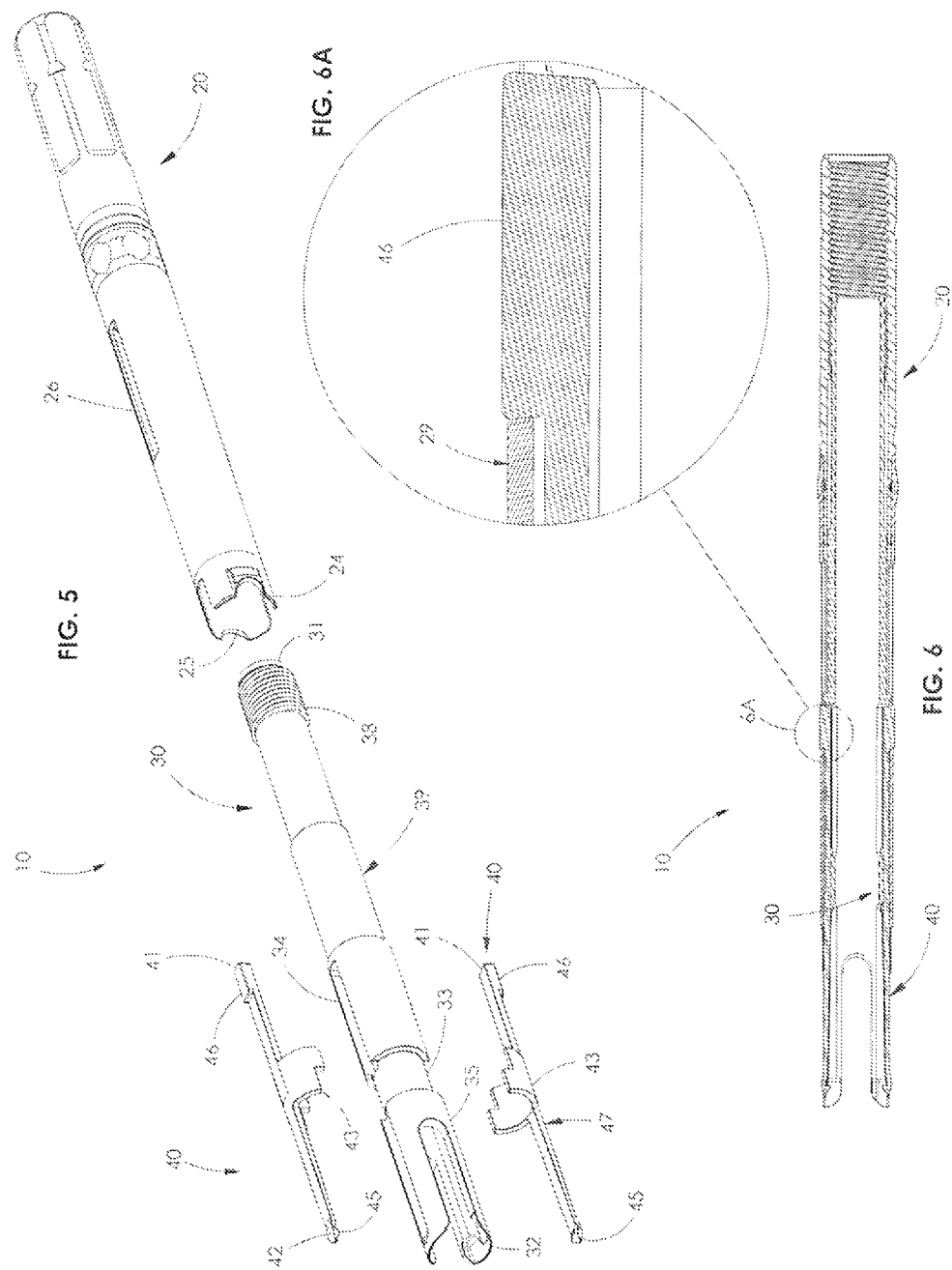

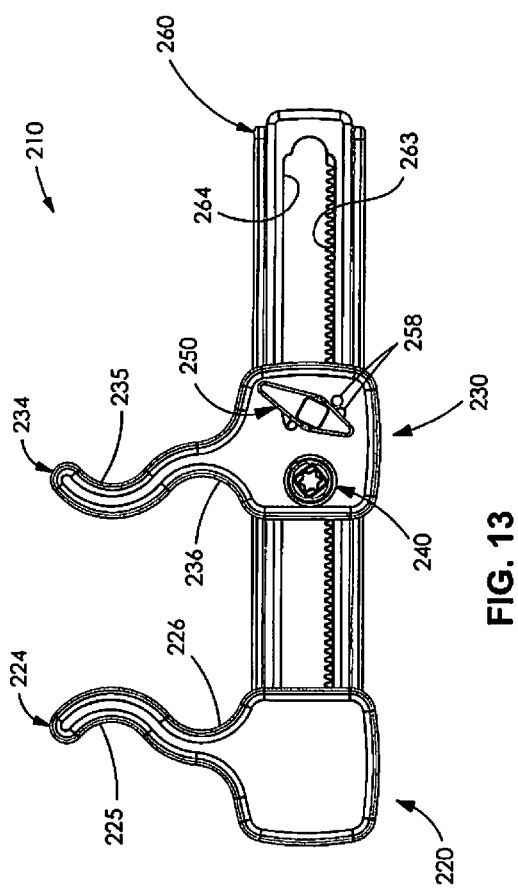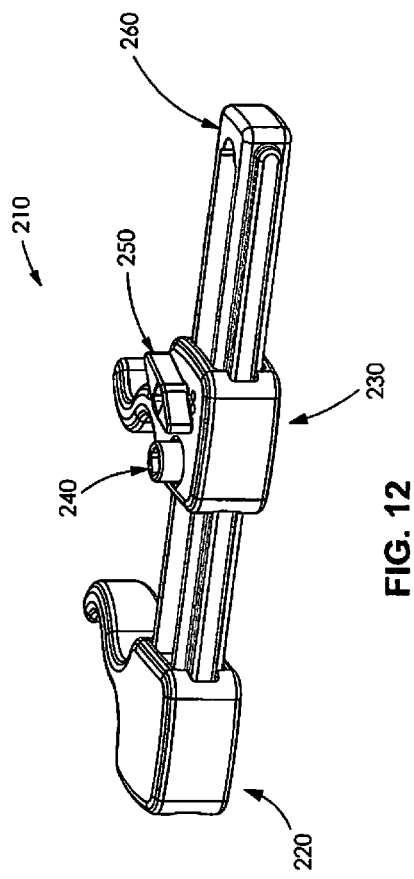

ROD REDUCER, COMPRESSOR, DISTRACTOR SYSTEM

CROSS-REFERENCE TO RELATED APPLICATION

The present application claims the benefit of, and priority to, U.S. Provisional Application Ser. No. 61/586,928, filed on Jan. 16, 2012, the contents of which is incorporated herein by reference in is entirety.

BACKGROUND

1. Technical Field

The present disclosure relates to a system and method for operating on the spine. More particularly, the present disclosure relates to a minimally invasive rod reducer, compressor/distractor system, and a method for using the compressor/distractor system to deliver a spinal rod to the head of a pedicle screw.

2. Background of Related Art

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury which restrict the range of motion of the spine or interfere with important elements of the nervous system. The problems include, but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include polyetheretherketone ("PEEK") interbody spacers, metal cages, and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. The opposing pair of longitudinally linked rods is commonly disposed along the long axis of the spine via a posterior approach. Pedicle screws are utilized to capture these rods and can be manufactured from any biocompatible material, including cobalt chrome, stainless steel, titanium, and PEEK. It is desired to perform these procedures in a minimally invasive manner to minimize pain and reduce recovery time for the patient. Therefore, a need exists for a minimally invasive rod reducer, compressor, distractor system that can deliver the rod into the head of the pedicle screw or bone anchor while maintaining the proper screw and rod construct alignment.

A rod reducer that is small enough in diameter to work with a minimally invasive retractor, such as the rod reducer disclosed in U.S. patent application Ser. No. 13/595,533, the contents of which are hereby incorporated by reference in their entirety and a minimally invasive retractor, such as the minimally invasive retractor disclosed in U.S. Pat. No. 7,846,093, the contents of which are hereby incorporated by reference in their entirety, are also disclosed.

SUMMARY

The present disclosure is directed towards a system for operating on the spine. The system includes pedicle screws, rod reducers, and a force applying device.

According to one aspect, the rod reducers include a proximal end and a distal end and define a longitudinal axis between the proximal and distal ends. The rod reducer includes an outer member and an inner member. The inner member is selectively attachable to the housing of the pedicle screw. The outer member is axially movable relative to the inner member when the inner member is secured to the housing of the pedicle screw to secure the spinal rod within the saddle of the housing of the pedicle screw. The outer member includes a proximal segment and a distal segment. The proximal segment is rotatable for axially translating the distal segment. The distal segment is engageable with the spinal rod to secure the spinal rod within the saddle upon the axial translation of the distal segment. The proximal segment independently rotates relative to the distal segment. The rod reducer includes a pair of gripping members configured to engage the housing of the pedicle screw. The pair of gripping members is positioned between the inner and outer members of the rod reducer.

The handle assembly is selectively engageable with the rod reducer to move the outer member of the rod reducer axially relative to the inner member of the rod reducer. The handle assembly is configured to rotate the outer member so that the rotational movement of the outer member axially moves the outer member relative to the inner member. The handle assembly includes a turning handle and an anti-torque handle. The anti-torque handle is selectively engageable with the proximal end of the rod reducer and the turning handle is selectively engageable with a proximal end of the anti-torque handle.

In another aspect, an embodiment of the system includes two rod reducers, a force applying device, and a fulcrum. The force applying device is configured for selectively engaging each rod reducer. The system may also include at least one minimally invasive retraction device.

In yet another aspect, the force applying device is a compressor/distractor device including a first hook member, a second hook member, and a body portion. The body portion has a first end and a track extending from the first end. The first end includes the first hook member in a fixed position. The first end may slidably receive the first hook member in a fixed position. The track includes a set of teeth and is configured for slidably receiving the second hook member.

The second hook member includes a switch assembly and a gear assembly. The second hook member traverses the track when the gear assembly is rotated. The gear assembly may also retain the second hook member within the track. The switch assembly permits the second hook member to traverse the track in a desired direction, towards the first hook member or away from the first hook member. The switch assembly may also restrain the second hook member from traversing the track in an undesired direction.

The first and second hook members may be configured in a compressing configuration to engage the two rod reducers such that rod reducers are between the hook members. The first and second hook members may also be configured in a distracting configuration to engage the rod reducers such that the hook members are between the rod reducers.

The fulcrum is configured to receive the proximal segment of the outer member of each rod reducer and remain in a fixed position on the longitudinal axis of each rod reducer.

According to still another aspect, a method for compressing or distracting vertebrae including two minimally invasive rod reducers, a compressor/distractor system, a spinal rod, and two pedicle screws. The method includes the steps of accessing the spinal area of a patient having at least two pedicle screws secured to respective vertebrae, engaging each pedicle screw with a rod reducer, advancing the spinal rod into the head of each pedicle screw, attaching a compressor/distractor device to each rod reducer, inserting a set screw through each rod reducer, manipulating the compressor/distractor device, and securing the spinal rod to each pedicle screw.

The method may also include the step of attaching a fulcrum to the proximal segment of each outer member before rotating the gear assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 1A is a perspective view of a minimally invasive rod reducer in accordance with the principles of the present disclosure before engagement with a rod and a pedicle screw;

FIG. 1B is a perspective view of the rod reducer of FIG. 1A after initial engagement of the rod and pedicle screw;

FIG. 1C is a perspective view of the rod reducer of FIG. 1B after the rod has been received by the shoulder portion of the pedicle screw FIG. 2 is a perspective view of the outer member of FIG. 1A;

FIG. 3 is a exploded view of the outer member of FIG. 2;

FIG. 4 is a bottom cross-sectional view of the outer member of FIG. 2 taken along the section line 4-4;

FIG. 5 is an exploded view of the rod reducer of FIG. 1A;

FIG. 6 is a side cross-sectional view of the of the rod reducer of FIG. 1A;

FIG. 6A is an enlarged view of the detail area 6A of FIG. 6;

FIG. 12 is an enlarged view of the compressor/distractor device of FIG. 9;

FIG. 13 is a top view of the compressor/distractor device of FIG. 12; and

DETAILED DESCRIPTION OF THE DRAWINGS

Figure 7B:
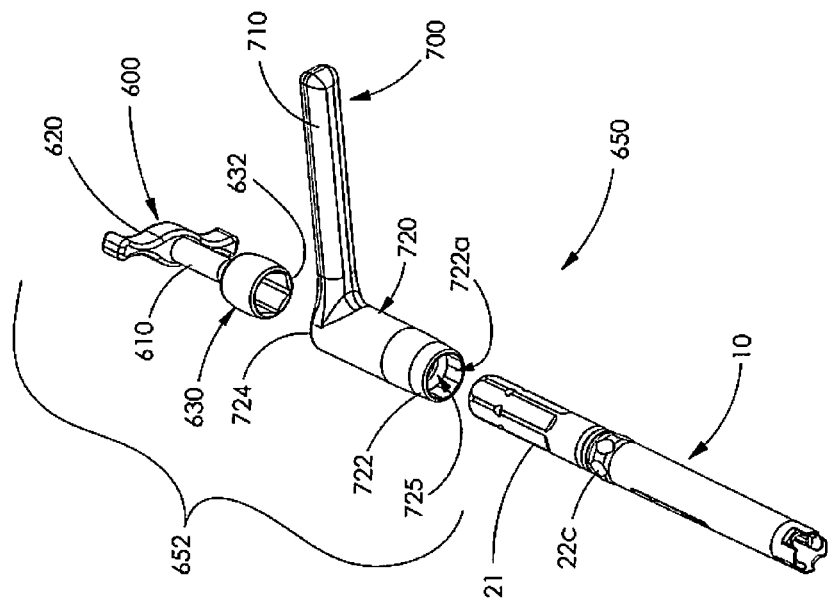
FIG. 7B is an exploded view of FIG. 7A.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" or "cranial" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Turning now to FIGS. 2-6A, a rod reducer 10 includes an outer member 20, an inner member 30, and a pair of gripping members 40, such as the rod reducer disclosed in U.S. patent application Ser. No. 13/595,533 which is incorporated by reference. Outer member 20 includes a proximal segment 21, a distal segment 22, and a ring member 27 that is disposed between proximal and distal segments 21, 22. Proximal segment 21 includes an engaging portion 21a at a distal end of proximal segment 21 and a gripping portion 21b at a proximal end of proximal segment 21. An inner surface 28 of proximal segment 21 is threaded. Distal segment 22 defines a slot 26 therethrough and includes a reducing portion 22a at a distal end of distal segment 22 and a receiving portion 22b at a proximal end of distal segment 22. Receiving portion 22b includes a plurality of gripping features 22c on an outer surface of receiving portion 22b. A pair of rod engaging slots 25 and a pair of gripping member receiving slots 24 are defined through reducing portion 22a. Receiving portion 22b of distal segment 22 is configured to receive engaging portion 21a of proximal segment 21 so that ring member 27 is disposed between proximal and distal segments 21, 22. The components of outer member 20 may be integrally formed or assembled.

Inner member 30 includes an elongate body member 39 that defines an annular recess 33 configured to receive the pair of gripping members 40 so that the gripping members 40 are disposed in opposition on the elongate body member 39. Inner member 30 includes a pair of arms 32 supported on a distal end of elongate body member 39. A proximal end of elongate body member 39 has a threaded arrangement 38 that mates with threaded inner surface 28 of proximal segment 21 of outer member 20 to axially advance outer member 20 relative to inner member 30 as will be described in greater detail below.

Each gripping member 40 includes a body 47 having a supporting member 43, a proximal finger 46, and a distal finger 45. Supporting member 43 is configured to engage annular recess 33 of inner member 30 to support body 47 of each gripping member 40 on inner member 30. Proximal finger 46 extends proximally from supporting member 43 and is slidably positionable within slot 26 of outer member 20. Distal finger 45 extends distally from supporting member 43 and is positionable between an arm 32 of inner member 30 and reducing portion 22a of outer member 20 so that distal finger 45 is substantially aligned with a gripping member receiving slot 24 of reducing portion 22a.

As illustrated in FIGS. 1A-1C, outer member 20 of rod reducer 10 is disposed in a proximal position relative to inner member 30 of rod reducer 10, distal fingers 45 of gripping member 40 of rod reducer 10 are secured to an outer surface of pedicle screw head 910. Proximal segment 21 of outer member 20 may then be rotated by virtue of the threaded arrangement between outer member 20 and inner member 30 for axially advancing distal segment 22 of outer member 20 relative to inner member 30 and proximal segment 21. Proximal segment 21 remains axially fixed when rotated. Notably, as proximal segment 21 rotates, distal segment 22 remains radially fixed as distal segment 22 axially translates relative to inner member 30 and proximal segment 21. Outer member 20 approximates a spinal rod 800 positioned between rod reducer 10 and pedicle screw 900 as outer member 20 is advanced toward pedicle screw 900 to secure spinal rod 800 within a saddle 912 of pedicle screw 900. As outer member 20 advances distally, a proximal end of slot 26 of outer member 20 approximates a proximal end of proximal fingers 46 of gripping member 40.

Figure 7A:
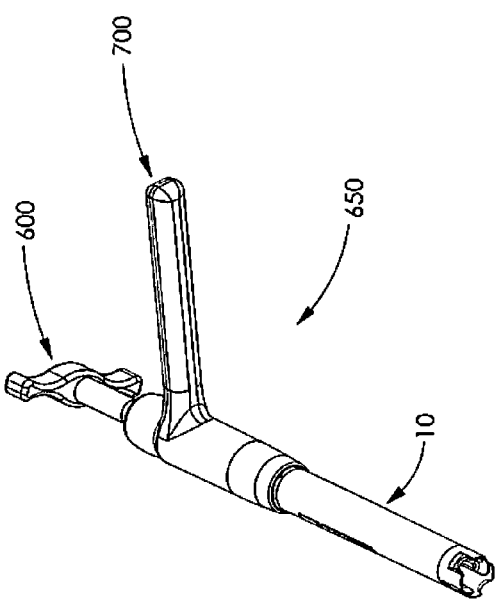
FIG. 7A is a perspective view of the outer member of FIG. 2 engaged with a turning handle and an anti-torque handle.

Turning now to FIGS. 7A and 7B, a rod reducer and handle assembly 650 includes the rod reducer 10 and a handle assembly 652. Handle assembly 652 includes a turning handle 600 and an anti-torque handle 700 that are selectively connectable to gripping portion 21b and gripping features 22c respectively on rod reducer 10. Turning handle 600 includes a shaft 610, a handle 620, and a socket 630 that defines an opening 632. Opening 632 is configured to receive a proximal end of gripping portion 21b of rod reducer 10. Handle 620 is secured to a proximal end of shaft 610 and a socket 630 that may be integrally formed is secured to a distal end of shaft 610. Anti-torque handle 700 includes a shaft 720 and a handle 710 that may be integrally formed. Shaft 720 includes a socket 722 that defines an opening 722a at a distal end of socket 722. Opening 722a is disposed in communication with a lumen 725 defined within shaft 720 and another opening 724 disposed at a proximal end of shaft 720 so that anti-torque handle 700 may slide over gripping portion 21b of rod reducer 10 and engage with gripping feature 22c of rod reducer 10 to prevent rotational movement of distal segment 22 of outer member 20 of rod reducer 10.

Thus, if needed, either or both the turning handle 600 and the anti-torque handle 700 may be used to facilitate the rotational movement of outer member 20 relative to inner member 30. In particular, rotation of turning handle 600 imparts rotational movement to proximal segment 21 of outer member 20 and anti-torque handle 700 imparts counter rotational movement to distal segment 22 of outer member 20 so that proximal segment 21 rotates and distal segment 22 axially translates without rotating. As appreciated, anti-torque handle 700 is configured to limit the amount of torque imparted from the rotational movement imparted by turning handle 600 to prevent undesirable torquing of the outer member 20. More particularly, anti-torque handle 700 slides down over the outer surface of outer member 20 of rod reducer 10 so that a distal end of anti-torque handle 700 engages distal segment 22 of outer member 20 and a proximal end of proximal segment 21 of outer member 20 is exposed for engagement with turning handle 600. Meanwhile, since gripping member 40 is secured within annular recess 33 of inner member 30 such that proximal finger 46 of gripping member 40 is supported in slot 26 of distal segment 22 of outer member 20, the engagement of anti-torque handle 700 with gripping feature 22c of distal segment 22 of outer member 20 prevents rotation of both distal segment 22 of outer member 20 and inner member 30 as proximal segment 21 of outer member 20 is rotated with turning handle 600. After spinal rod 800 is fully reduced into the saddle 910 of pedicle screw 900, turning handle 600 and anti-torque handle 700 may be removed and a set screw (not shown) may be inserted down an inner diameter of rod reducer 10 to lock spinal rod 800 into place. Alternatively, anti-torque handle 700 may also be used to prevent rotation when tightening the set screw after spinal rod 800 has been fully reduced. Rod reducer 10 may then be removed.

Figure 8:
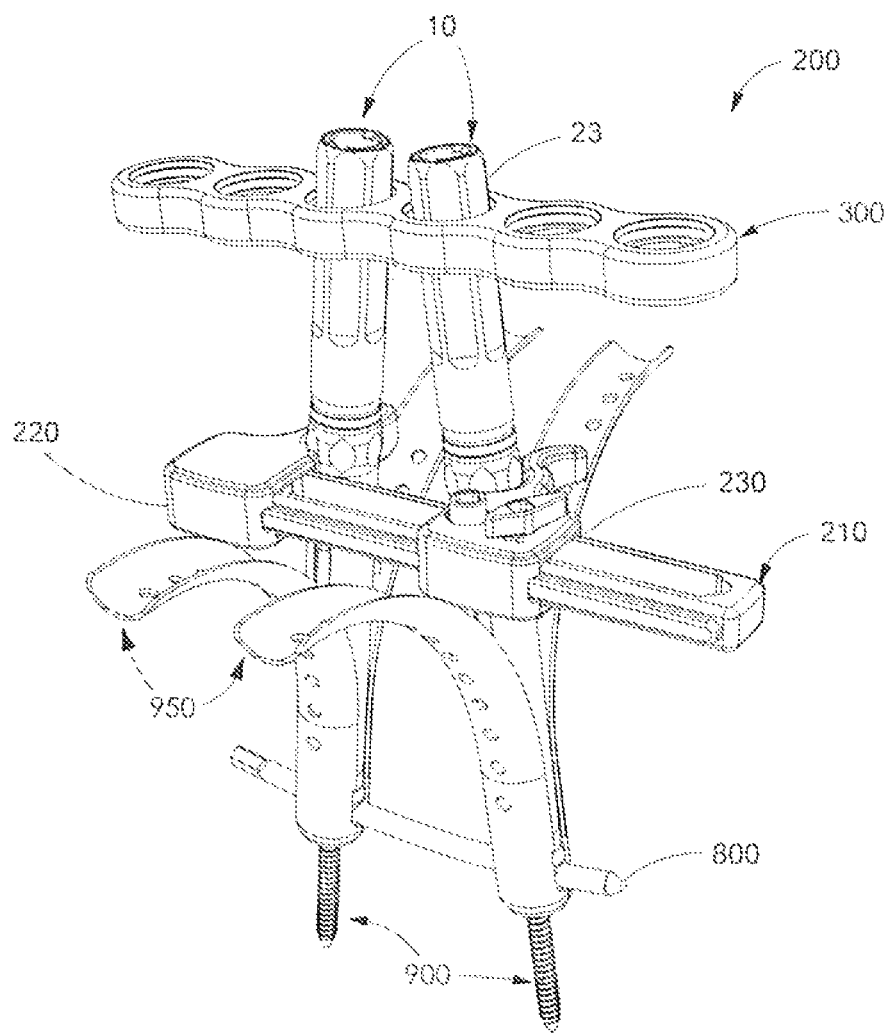
FIG. 8 is a perspective view of an embodiment of a compressor/distractor system in accordance with the principles of the present disclosure in a compressing configuration.
Figure 9:
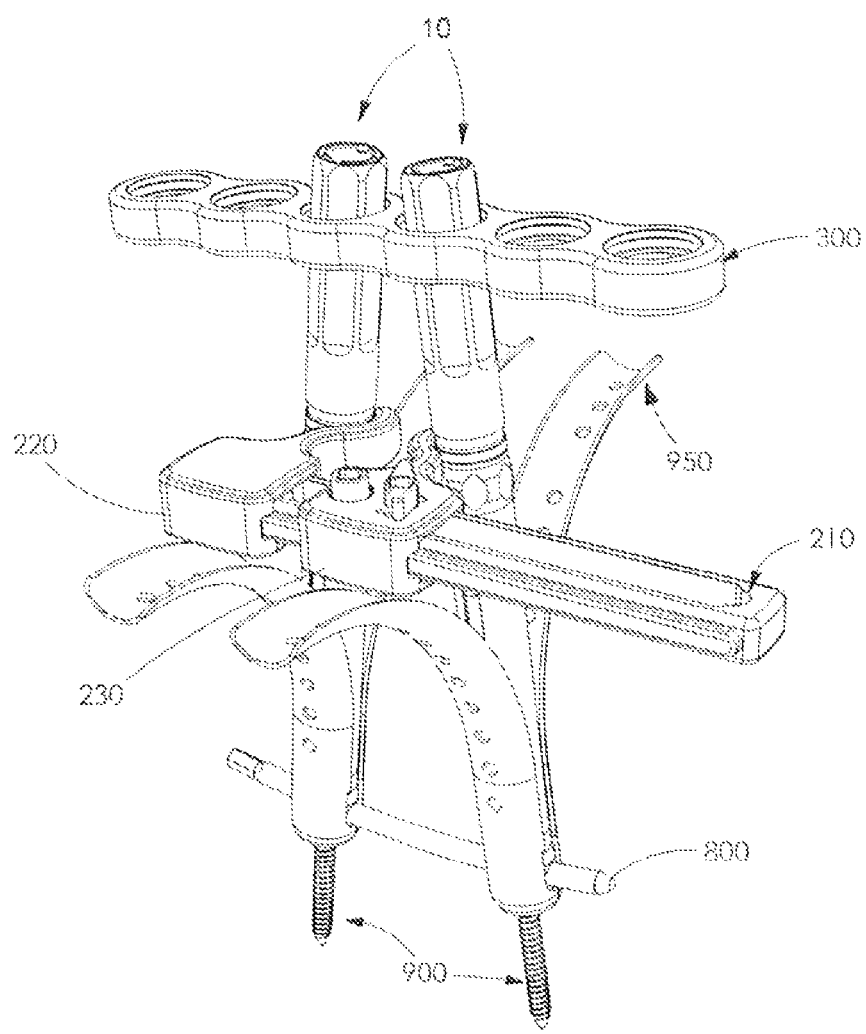
FIG. 9 is a perspective view of the compressor/distractor system of FIG. 8 in a distracting configuration.

Referring now to FIGS. 8 and 9, a compressor/distractor system 200 includes rod reducers 10, a compressor/distractor device 210, and a fulcrum 300. System 200 may further include one or more minimally invasive retraction devices 950, such as the retractor disclosed in U.S. Pat. No. 7,846,093, the entire contents of which is incorporated by reference. Each of the two rod reducers 10 engages a respective pedicle screw 900. Each pedicle screw 900 is inserted into a respective vertebra and is configured to receive spinal rod 800 in saddle portion 912 as shown in FIG. 1C. Compressor/distractor device 210 is configured for selective engagement with each rod reducer 10 when each rod reducer 10 is attached to pedicle screw 900.

Figure 10A:
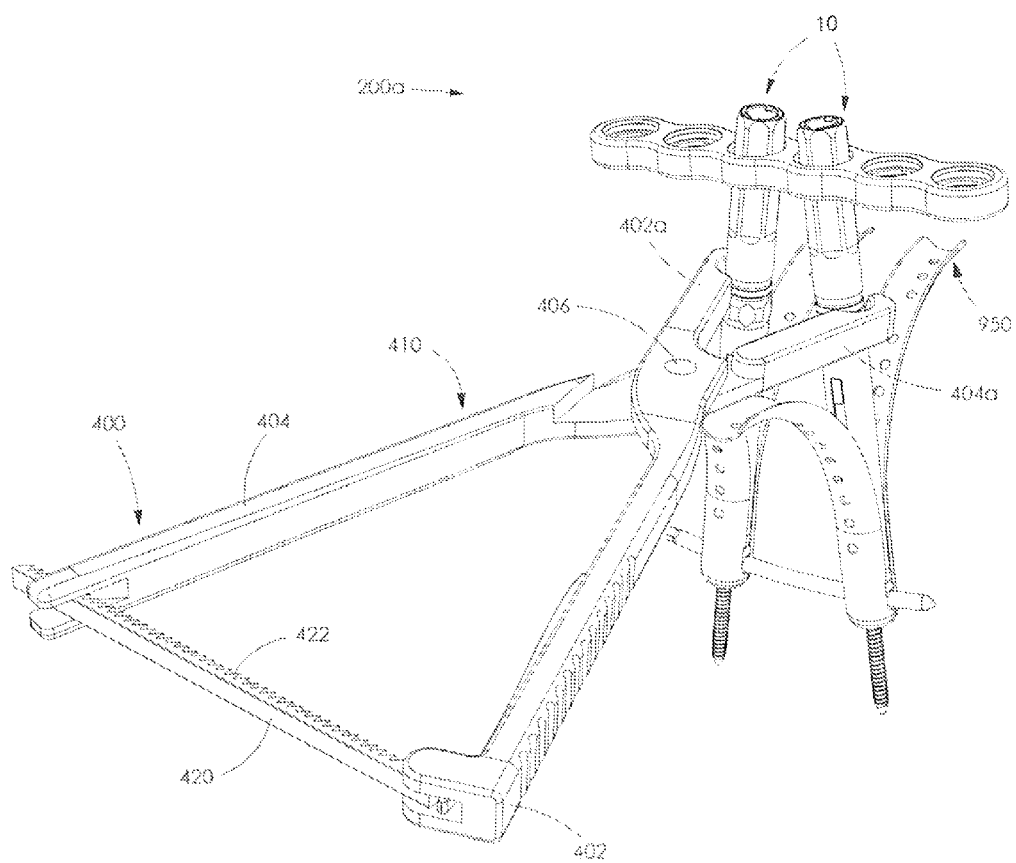
FIG. 10A is a perspective view of another embodiment of a compressor/distractor system in accordance with the principles of the present disclosure in a compressing configuration.
Figure 10B:
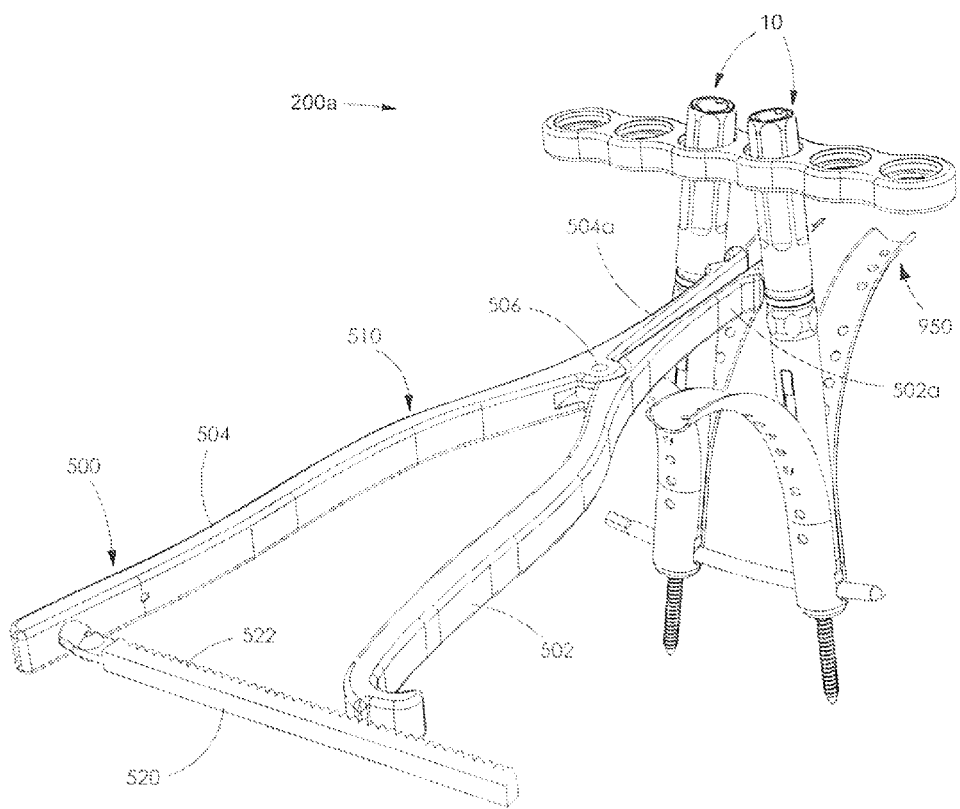
FIG. 10B is a perspective view of the compressor/distractor system of FIG. 10A in a distracting configuration.

FIGS. 10A and 10B illustrate other embodiments of compressor/distractor system 200a using compressor 400 and distractor 500 respectively as the force applying device. As shown in FIG. 10A, the compressor 400 has a handle assembly 410 with handles 402, 404 that are pivotably coupled together by pivot pin 406. Distal portions of handles 402, 404 have respective grippers 402a, 404a for engaging rod reducers 10. Each gripper 402a, 404a includes an arcuate recess configured for engaging an outer surface of rod reducer 10. Compressor 400 also includes an arm 420 having teeth 422 disposed thereon. Teeth 422 releasably engage a distal portion of handle 404 for maintaining a predetermined distance or spacing between handles 402, 404 during a compression stroke that moves rod reducers 10 towards each other. The arm 420 is pivotably coupled to a distal end of arm 402 such that it can be repositioned and allow handles 402, 404 to be moved away from each other once the desired amount of compression is achieved. Similarly, as shown in FIG. 10B, the distractor 500 has a handle assembly 510 with handles 502, 504 that are pivotably coupled together by pivot pin 506.

Distal portions of handles 502, 504 have respective grippers 502a, 504a for engaging rod reducers 10. Each gripper 502a, 504a includes an arcuate recess configured for engaging an outer surface of rod reducer 10. Distractor 500 also includes an arm 520 having teeth 522 disposed thereon. Teeth 522 releasably engage a distal portion of handle 502 for maintaining a predetermined distance or spacing between handles 502, 504 during a distraction stroke that moves rod reducers 10 away from each other. The arm 520 is pivotably coupled to a distal end of arm 504 such that it can be repositioned and allow handles 502, 504 to be moved away from each other once the desired amount of distraction is achieved.

Figure 11A:
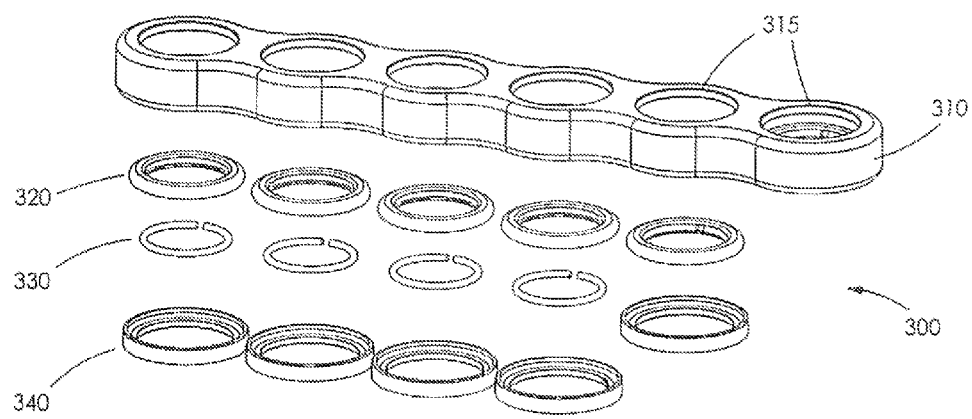
FIG. 11A is an exploded view of the fulcrum of FIG. 11.
Figure 11:
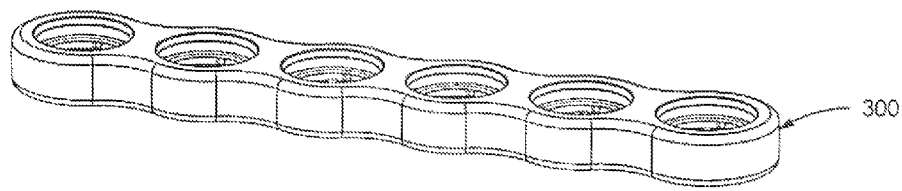
FIG. 11 is a perspective view of the fulcrum of FIG. 9.
Figure 11B:
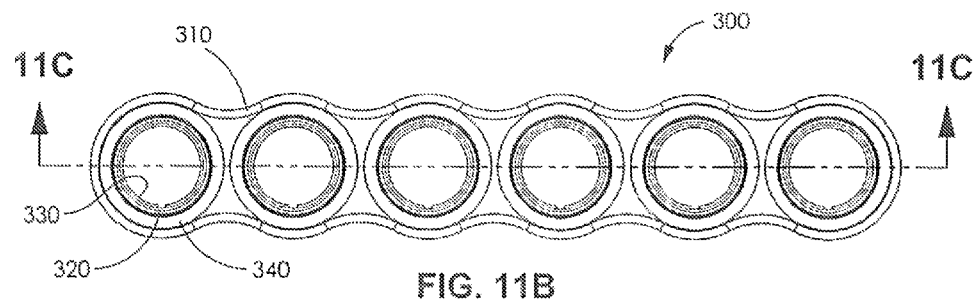
FIG. 11B is a top view of the fulcrum of FIG. 11.
Figure 11C:
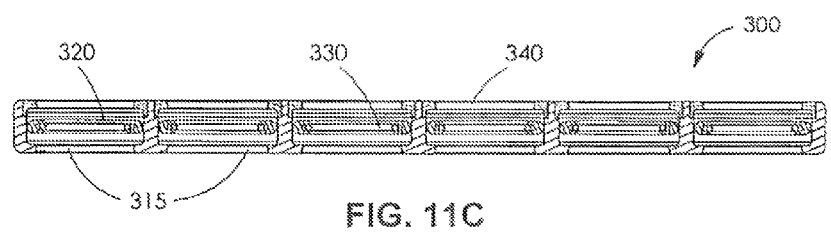
FIG. 11C is a side cross-sectional view of the fulcrum taken along the section line 11C-11C in FIG. 11B.

Now referring to FIGS. 11-11C illustrating fulcrum 300 including through holes 315 which receive inner bearing rings 320 which house retaining rings 330 that are prevented from falling out of fulcrum 300 by caps 340. Fulcrum 300 is an elongate structure and each through hole 315 includes an annular groove for retaining inner bearing rings 320 and their respective retaining rings 330.

Figure 14:
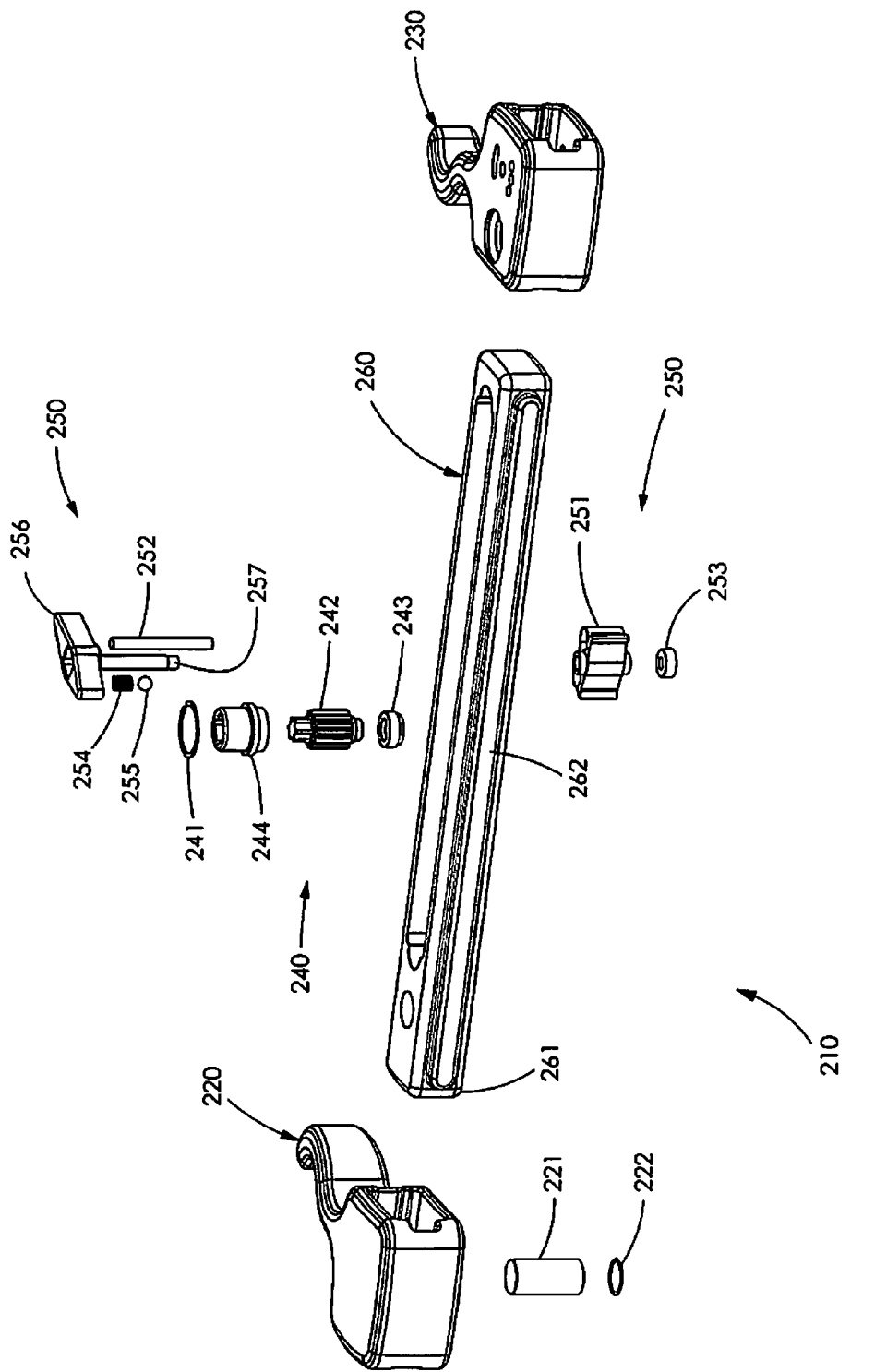
FIG. 14 is an exploded view of the compressor/distractor device of FIG. 12.

Referring now to FIGS. 12-14, compressor/distractor device 210 has a first hook member 220, a second hook member 230, and a body portion 260. Body portion 260 includes first end 261 and track 262 extending from first end 261 along a length of body portion 260. Track 262 includes a set of teeth 263 and sidewall 264. First end 261 is insertable into a recess of the first hook member 220 and is fixed in position at first end 261 of body portion 260 by the cooperation of retaining pin 221 and first end retaining ring 222.

First and second hook members 220, 230 may each include hook portions 224, 234 for engaging rod reducers 10. Hook portions 224, 234 have respective distracting hooks 225, 235 and compressing hooks 226, 236. When rod reducers 10 are between first and second hook members 220, 230, each compressing hook 226, 236 engages a rod reducer 10 in a compressing configuration of compressor/distractor device 210 (FIG. 8). When first and second hook members 220, 230 are between rod reducers 10, each distracting hook 225, 235 engages a rod reducer 10 in a distracting configuration of compressor/distractor device 210 (FIG. 9). Compressor/distractor device 210 may also have a neutral configuration. Each hook member 220, 230 may engage gripping features 22c of each rod reducer 10.

Second hook member 230 may include a switch assembly 250 and a gear assembly 240. Switch assembly 250 may include a pawl 251, a pawl switch pin 252, a switch cap 253, a spring 254, a ball 255, ball detents 258, a switch 256, and a switch shaft 257. Switch assembly 250 is selectable amongst a first condition, a second condition, and a third condition. Each condition may correspond to a configuration of the compressor/distractor device 210. In the first condition, switch assembly 250 restrains second hook member 230 from traversing track 262 towards the first hook member 220, while permitting second hook member 230 to traverse track 262 away from the first hook member 220 (i.e., a distracting configuration). In the second condition, switch assembly 250 restrains second hook member 230 from traversing track 262 away from the first hook member 220, while permitting second hook member 230 to traverse track 262 towards the first hook member 220 (i.e., a compressing configuration). In the third condition, switch assembly 250 allows the second hook member 230 to freely move along track 262 in either direction (i.e., a neutral configuration), which allows for quick adjustment of compressor/distractor device 210.

Switch 256 rotates about switch shaft 257 causing pawl pivot pin 252 to rotate pawl 251 about switch shaft 257. Pawl pivot pin 252 acts on pawl 251 causing pawl 251 to engage set of teeth 263 which restrains second hook member from traversing in the undesired direction.

Second hook member 230 may include ball detents 258. Each ball detent 258 corresponds to a position of switch 256. Switch 256 may be retained in each position by spring 254 pressing ball 255 into a corresponding ball detent 258. Ball 255 selectively engages each ball detent 258 when the switch is in one of the positions corresponding to the compressing, distracting, and neutral configurations of the compressor/distractor device 210.

Gear assembly 240 engages set of teeth 263 causing second hook member 230 to traverse track 262. Rotation of traversing screw 244 rotates pinion 242. The cooperation of pinion 242 with set of teeth 263 induces the second hook member 230 to traverse track 262. A drive tool (not shown) may engage and rotate traversing screw 244.

A method for using system 200 to manipulate a vertebra into a desired position with respect to a second vertebra is discussed below. First, a surgeon accesses the spinal area of a patient having at least two pedicle screws 900 secured to adjacent vertebrae (not shown). Each pedicle screw 900 may be engaged by a minimally invasive retraction device 950. The surgeon then engages each pedicle screw 900 with a rod reducer 10 by attaching inner member 30 to pedicle screw head 910 as shown in FIG. 1B. Each inner member 30 receives a respective pedicle screw head 910 between arms 32. Next, the surgeon advances an outer member 20 along each inner member 30 by rotating the distal segment 21 of the outer member 20. The surgeon may use handle assembly 650 to rotate distal segment 21.

Rod engaging slots 25 of proximal segment 22 of each outer member 20 receives a portion of rod 800 and advances rod 800 into saddle portion 912 of each pedicle screw 900 as shown in FIGS. 1B and 1C. Once each outer member 20 is fully advanced with respect to each inner member 30 as shown in FIG. 1C, the surgeon engages each outer member 20 with a force applying device 210, 400, 500 as shown in FIGS. 8-10B. The force applying device may include gear assembly 240. Then the surgeon inserts a set screw (not shown) through each rod reducer 10 for securing the rod 800 to each pedicle screw 900. The surgeon may rotate at least one of the set screws to either partially or fully secure rod 800 to at least one of the pedicle screws 900.

Then the surgeon manipulates gear assembly 240 until each pedicle screw 900 is in a desired position on rod 800. Manipulation of gear assembly 240 may include rotating traversing screw 244. The surgeon may use a drive tool to manipulate gear assembly 240.

Then the surgeon rotates each set screw to fully secure rod 800 to each pedicle screw 900 in the desired position. Then the surgeon may remove compressor/distractor device 210 and each rod reducer 10.

The surgeon may also attach fulcrum 300 to gripping portion 21b of proximal segment 21 of each outer member 20 before manipulating gear assembly 240. Fulcrum 300 may then be removed with the compressor/distractor device 210 and each of the rod reducers 10.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A compressor/distractor system comprising:
   two rod reducers each including a proximal end and a distal end and defining a longitudinal axis between the proximal and distal ends, each rod reducer including an outer member and an inner member, the inner member being selectively attachable to a head of a pedicle screw, the outer member being axially movable relative to the inner member when the inner member is secured to the head of the pedicle screw to secure a spinal rod within a saddle portion of the head of the pedicle screw;
   a force applying device which selectively engages each of the two rod reducers, the force applying device including first and second hook members, the force applying device having a compressing configuration when the first and second hook members engage the two rod reducers with the rod reducers positioned between the first and second hook members and having a distracting configuration when the first and second hook members engage the two rod reducers with the first and second hook members positioned between the two rod reducers; and
   a fulcrum which engages the proximal end of each of the two rod reducers and remains in a fixed position on the longitudinal axis of each of the two rod reducers.

2. The compressor/distractor system of claim 1, wherein the second hook member has a switch assembly and a gear assembly, and wherein the force applying device includes a body portion having a first end and a track extending from the first end, the first end having the first hook member in a fixed position, the track having a set of teeth and configured to slidably receive the second hook member, the second hook member traverses the track when the gear assembly cooperates with the set of teeth, the switch assembly selectively engages the set of teeth restraining the second hook member from traversing the track in a first direction.

3. The compressor/distractor system of claim 2, wherein the first and second hook members engage a gripping portion on each rod reducer.

4. The compressor/distractor system of claim 2, wherein the gear assembly includes a pinion which cooperates with the set of teeth and receives a screw which rotates the pinion.

5. The compressor/distractor system of claim 2, wherein the switch assembly includes a switch, a pawl having a pawl pivot pin, and a switch shaft, the rotation of the switch causes the pawl pivot pin to rotate the pawl about the switch shaft.

6. The compressor/distractor system of claim 5, wherein the rotation of the pawl about the switch shaft causes the pawl to engage the set of teeth restraining the second hook member from traversing the track in the first direction.

7. The compressor/distractor system of claim 1, wherein the fulcrum includes a plurality of through holes, each of the through holes configured to receive the distal end of each rod reducer.

8. The compressor/distractor system of claim 1, wherein a distance defined between the fixed position on the longitudinal axis of each of the two rod reducers engaged by the fulcrum is constant when the force applying device compresses and distracts the rod reducers relative to one another.

9. The compressor/distractor system of claim 1, wherein each of the first and second hook members has a hook portion including a distracting hook and a compressing hook.

10. A compressor/distractor system comprising:
    two rod reducers each including a proximal end and a distal end and defining a longitudinal axis between the proximal and distal ends, each rod reducer including an outer member and an inner member, the inner member being selectively attachable to a head of a pedicle screw, the outer member being axially movable relative to the inner member when the inner member is secured to the head of the pedicle screw to secure a spinal rod within a saddle portion of the head of the pedicle screw;
    a force applying device which selectively engages each of the two rod reducers, the force applying device including:
      a first hook member;
      a second hook member having a switch assembly and a gear assembly; and
      a body portion having a first end and a track extending from the first end, the first end having the first hook member in a fixed position, the track having a set of teeth and configured to slidably receive the second hook member, the second hook member traverses the track when the gear assembly cooperates with the set of teeth, the switch assembly selectively engages the set of teeth restraining the second hook member from traversing the track in a first direction, wherein the force applying device has a compressing configuration, a distracting configuration, and a neutral configuration and the second hook member includes ball detents each corresponding to a first, a second, and a third position of the switch assembly, each position of the switch assembly corresponding to a respective configuration of the force applying device; and
    a fulcrum which engages the proximal end of each of the two rod reducers and remains in a fixed position on the longitudinal axis of each of the two rod reducers.

11. The compressor/distractor system of claim 10, wherein the switch assembly includes a spring and a ball, the spring mounted to the switch and configured to press the ball into the ball detents, the ball selectively engages a ball detent when the switch is in each position.

12. A compressor/distractor system comprising:
    two rod reducers each including a proximal end and a distal end and defining a longitudinal axis between the proximal and distal ends, each rod reducer including an outer member and an inner member, the inner member being selectively attachable to a head of a pedicle screw, the outer member being axially movable relative to the inner member when the inner member is secured to the head of the pedicle screw to secure a spinal rod within a saddle portion of the head of the pedicle screw;
    a force applying device which selectively engages each of the two rod reducers, the force applying device including:
      a first hook member having a hook portion including a distracting hook and a compressing hook;
      a second hook member having a switch assembly, a gear assembly and a hook portion including a distracting hook and a compressing hook; and
      a body portion having a first end and a track extending from the first end, the first end having the first hook member in a fixed position, the track having a set of teeth and configured to slidably receive the second hook member, the second hook member traverses the track when the gear assembly cooperates with the set of teeth, the switch assembly selectively engages the set of teeth restraining the second hook member from traversing the track in a first direction; and
    a fulcrum which engages the proximal end of each of the two rod reducers and remains in a fixed position on the longitudinal axis of each of the two rod reducers.

* * * * *